US00PP24194P2

(12) United States Plant Patent
Horvath

(10) Patent No.: US PP24,194 P2
(45) Date of Patent: Jan. 21, 2014

(54) ***SEDUM* PLANT NAMED 'PURE JOY'**

(50) Latin Name: ***Sedum* hybrid**
Varietal Denomination: Pure Joy

(76) Inventor: Brent Horvath, Fontana, WI (US)

( * ) Notice: Subject to any disclaimer, the term of this patent is extended or adjusted under 35 U.S.C. 154(b) by 120 days.

(21) Appl. No.: 13/200,018

(22) Filed: Sep. 16, 2011

(51) Int. Cl.
*A01H 5/00* (2006.01)

(52) U.S. Cl.
USPC ..... Plt./479

(58) Field of Classification Search
USPC ..... Plt./479
See application file for complete search history.

*Primary Examiner* — Kent L Bell

(57) ABSTRACT

A new, distinct *Sedum* plant as shown and described, characterized by larger grey green foliage, pink bi-color flowers, taller height, extra number of flowers per stem, and a compact mounding habit compared to the seed parent.

2 Drawing Sheets

Latin name: *Sedum* hybrid.
Cultivar name: 'Pure Joy'.

BACKGROUND OF THE INVENTION

The present invention relates to a new and distinct hybrid of *Sedum* plant named 'Pure Joy' characterized by larger grey green foliage, pink bi-color flowers, taller height, extra number of flowers per stem, and a compact mounding habit compared to the seed parent. The new *Sedum* was raised as a seedling from open pollinated seed sown from an unnamed *Sedum tatranowii*, not patented, in Hebron, Ill. in 2005. The selection of the new plant was due to its' larger grey green foliage, pink bi-color flowers, taller height, extra number of flowers per stem, and a compact mounding habit compared to the seed parent. Initial asexual reproduction has taken place at a nursery in Hebron, Ill. since 2006 by means of division, and vegetative cuttings. The new *Sedum* has shown to be stable and identical in reproduction to the originally discovered plant after rooting over 1400 plants from 2006 to 2011.

SUMMARY OF THE INVENTION

The new *Sedum* plant named 'Pure Joy' characterized by larger grey green foliage, pink bi-color flowers, taller height, extra number of flowers per stem, and a compact mounding habit compared to the seed parent have been observed to be unique and stable.

Plants of the new *Sedum* can be compared to plants of *Sedum spectabile* 'Brilliant' not patented. 1. The new *Sedum* plant is a hybrid and does not produce seed while *Sedum spectabile* is fertile and produces seed. 2. The new *Sedum* plant has a mature size measuring 25-30 cm high and up to 50 cm wide while *Sedum spectabile* measures 45-55 cm high and 55-65 cm wide. 3. The new *Sedum* has pink bi-color flowers while *Sedum spectabile* is entirely pink.

Plants of the new *Sedum* can also be compared to the seed parent plant, an unnamed *Sedum tatranowii*, not patented. 1. The new plant is a hybrid and does not produce seed while the seed parent plant is fertile and produces viable seed. 2. The new *Sedum* has a mature size of 25-30 cm high and 50 cm wide while the seed parent has a mature size of 12 cm high and 30 cm wide. 3. The new *Sedum* has larger foliage measuring on average up to 5-6 cm long by 2 cm wide while the seed parent has foliage measuring 6 mm across by 2 cm long. 4. The new *Sedum* has a stem diameter of 6-7 mm while the seed parent has stem diameter of 2 mm. 5. The new *Sedum* has pink bi-color flowers, compared to the mostly white flowers of the seed parent.

DESCRIPTION OF PHOTOGRAPHS

Figure 1:
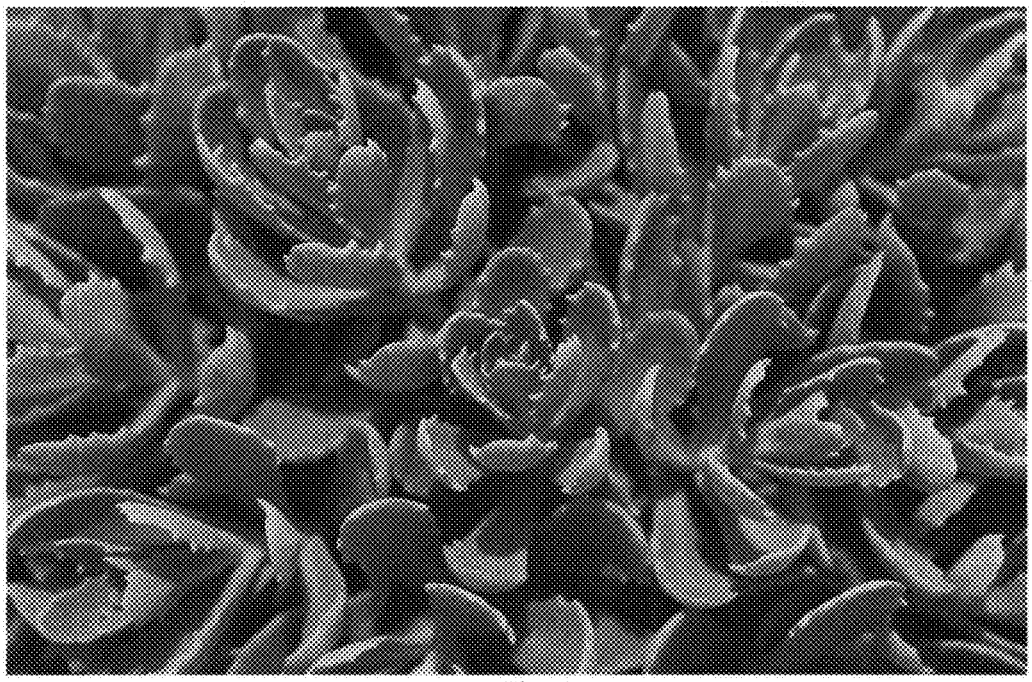
Figure 2:
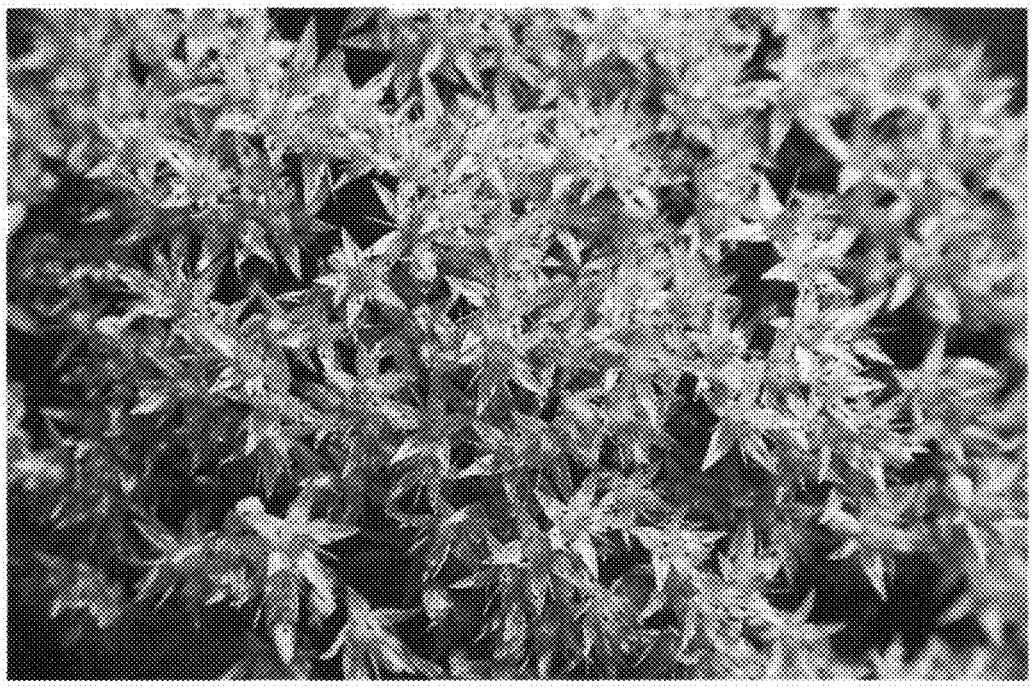
Figure 3:
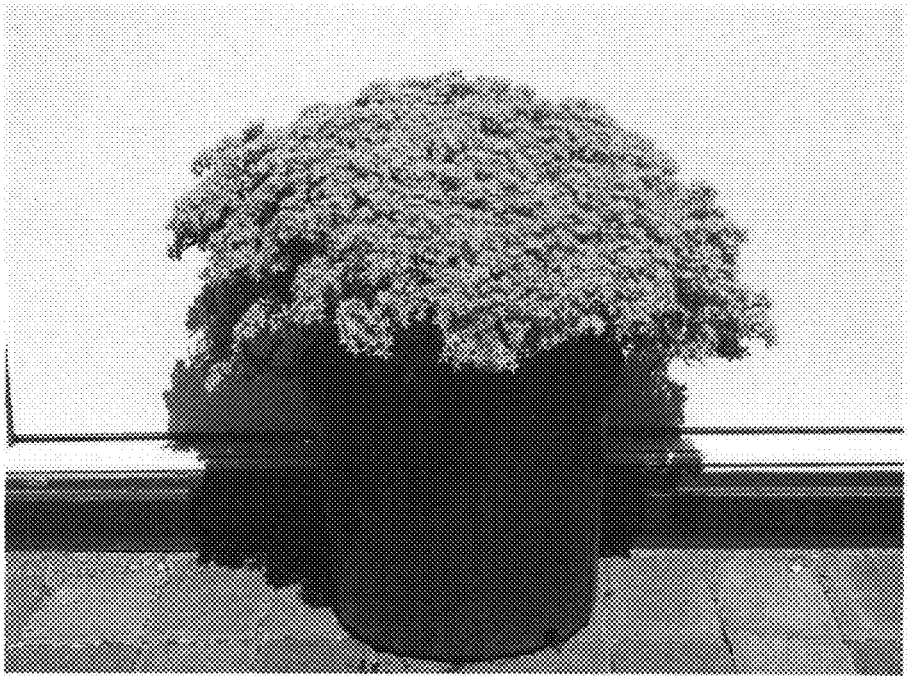

Plants pictured in the drawing were grown for three years.
FIG. 1. Close up of the foliage.
FIG. 2. Close up of the flowers.
FIG. 3. A single plant in September.

DETAILED BOTANICAL DESCRIPTION

In the following description, color references are made to The Royal Horticultural Society Colour Chart (2001). Plants used for the description were grown for three years at a nursery in Hebron, Ill. USA. Measurements and numerical values represent averages of typical plants.

Botanical classification: *Sedum* hybrid cultivar Pure Joy.

Parentage: Male or pollen unknown and female or seed an open pollinated, unnamed *Sedum tatranowii*.

Propagation: Vegetative division and cutting propagation.

Plant description: Overall habit of the new *Sedum* is basal clumps, with upright stems topped by pink bi-color flowers in August and September. Growth rate of the new *Sedum* plant is moderately vigorous.

*Plant height.*—Average 25-30 cm.
*Plant width.*—Up to 50 cm.
*Stem color.*—144 A.
*Stem shape.*—Both typical and observed — round.
*Stem texture.*—Glabrous.
*Stem length.*—25-30 cm.
*Stem diameter.*—6-7 mm.
*Internode length.*—7 mm.

Foliage:

*Type.*—Deciduous.
*Shape.*—Obovate.
*Petiole.*—None.
*Length.*—5-6 cm.
*Width.*—2 cm.

*Thickness.*—1-2 mm.
*Margin.*—Dentate.
*Leaf apex, typical and observed.*—Obtuse.
*Leaf bases, typical and observed.*—Cuneate.
*Texture.*—Smooth.
*Leaf arrangement.*—Alternate, crowded except at the base of the stems.
*Leaf venation pattern.*—None noticed.
*Leaf vein color.*—None noticed.
*Adaxial leaf description.*—Color is 137 B.
*Abaxial leaf description.*—Color is 137 D.
*Fall foliage color.*—None noticed.

Flower:

*Petal count.*—5.
*Petal shape.*—Lanceolate.
*Adaxial petal color.*—62 C.
*Abaxial petal color.*—65 D.
*Petal apex shape.*—Acuminate.
*Petal base.*—3 mm wide.
*Petal length.*—6 mm.
*Petal width.*—3 mm.
*Petal margin, typical and observed.*—Entire.
*Petal bases, typical and observed.*—Obtuse.
*Inflorescence type.*—Panicle on basal flowering stems.
*Panicle color.*—As a whole the color is close to 62 C.
*Inflorescence size.*—12 cm across, 6 mm tall.
*Inflorescence length.*—6 mm.
*Inflorescence width.*—12 cm.
*Flower number.*—Approximately 1500 per panicle.
*Bloom period and duration.*—Mid August to Mid September, lasting three to four weeks.
*Bud shape, typical and observed.*—Elliptical.
*Bud length, typical and observed.*—3 mm.
*Bud diameter, typical and observed.*—Close to 2 mm.
*Bud color, typical and observed.*—Close to 150 D.
*Sepal size.*—1 mm across, 2 mm tall.
*Sepal number.*—5.
*Sepal shape, typical and observed.*—Narrow ovate.
*Sepal apex, typical and observed.*—Acute.
*Sepal margin, typical and observed.*—Entire.
*Sepal color, abaxial and adaxial typical and observed.*—Close to 138 D.
*Peduncle length, typical and observed.*—25 mm.
*Peduncle diameter, typical and observed.*—1 mm.
*Peduncle color, typical and observed.*—Close to N 199 C.
*Pedicel length, typical and observed.*—2 mm.
*Pedicel diameter, typical and observed.*—Less than 1 mm.
*Pedicel color, typical and observed.*—Close to 146 C.
*Carpel color.*—N 74 A at the tips fading to white at the base.
*Carpel surfaces.*—Glabrous.
*Stigma shape.*—Capitate.
*Stigma size.*—1-2 mm.
*Style length.*—1 mm.
*Style shape.*—Slender.
*Ovary size.*—1 mm.
*Ovary shape.*—Cordate.
*Fertility.*—Sterile, 5 anthers no pollen, 5 stamens at 5 mm long. Anthers can appear dark in color as they do in the FIG. 2. of the drawings.
*Blooming habit.*—Domed, terminal panicle on up to 25-30 cm stems.
*Scent.*—No scent noticed.
*Fruit.*—None.
*Hardiness.*—U.S.D.A. hardiness zones 4-9.
*Disease resistance.*—Resistance to diseases common to *Sedum* has not been observed on plants grown under nursery conditions.
*Pest resistance.*—Resistance to pests common to *Sedum* has not been observed on plants grown under nursery conditions.

I claim:

1. A new, distinct *Sedum* plant as shown and described, characterized by larger grey green foliage, pink bi-color flowers, taller height, extra number of flowers per stem, and a compact mounding habit compared to the seed parent.

* * * * *